(12) United States Patent
Sawhney

(10) Patent No.: US 7,025,990 B2
(45) Date of Patent: *Apr. 11, 2006

(54) METHODS FOR FORMING REGIONAL TISSUE ADHERENT BARRIERS AND DRUG DELIVERY SYSTEMS

(75) Inventor: Amarpreet S. Sawhney, Bedford, MA (US)

(73) Assignee: Incept LLC, Lexington, MA (US)

( * ) Notice: Subject to any disclaimer, the term of this patent is extended or adjusted under 35 U.S.C. 154(b) by 379 days.

This patent is subject to a terminal disclaimer.

(21) Appl. No.: 10/266,980

(22) Filed: Oct. 8, 2002

(65) Prior Publication Data

US 2003/0077242 A1 Apr. 24, 2003

Related U.S. Application Data

(63) Continuation of application No. 09/134,748, filed on Aug. 14, 1998, now Pat. No. 6,514,534.

(51) Int. Cl.
*A61K 9/10* (2006.01)
*A61K 47/32* (2006.01)

(52) U.S. Cl. ........................ 424/486; 424/487; 514/944

(58) Field of Classification Search ................. 424/486, 424/487; 514/944
See application file for complete search history.

(56) References Cited

U.S. PATENT DOCUMENTS

| | | | |
|---|---|---|---|
| 3,991,766 A | 11/1976 | Schmitt et al. .......... 128/335.5 |
| 4,101,380 A | 7/1978 | Rubinstein et al. ............ 195/63 |
| 4,141,973 A | 2/1979 | Balazs ........................ 424/180 |
| 4,450,150 A | 5/1984 | Sidman ....................... 424/1.1 |
| 4,511,478 A | 4/1985 | Nowinski et al. ............ 210/691 |
| 4,532,134 A | 7/1985 | Malette et al. ................. 514/55 |
| 4,762,129 A | 8/1988 | Bonzel ........................ 128/344 |
| 4,886,787 A | 12/1989 | de Belder et al. ............. 514/57 |
| 4,894,238 A | 1/1990 | Embry et al. ................ 424/486 |
| 4,911,926 A | 3/1990 | Henry et al. ................. 424/426 |
| 4,994,277 A | 2/1991 | Higham et al. .............. 424/443 |
| 5,093,319 A | 3/1992 | Higham et al. ................ 514/55 |
| 5,126,141 A | 6/1992 | Henry ........................ 424/423 |
| 5,140,016 A | 8/1992 | Goldberg et al. .............. 514/57 |
| 5,162,430 A | 11/1992 | Rhee et al. ................. 525/54.1 |
| 5,171,148 A | 12/1992 | Wasserman et al. ......... 433/215 |
| 5,190,759 A | 3/1993 | Lindblad et al. ............. 424/423 |
| 5,198,220 A | 3/1993 | Damani ....................... 424/426 |
| 5,246,698 A | 9/1993 | Leshchiner et al. ....... 424/78.08 |
| 5,266,326 A | 11/1993 | Barry et al. ................. 424/423 |
| 5,324,775 A | 6/1994 | Rhee et al. ................. 525/54.2 |
| 5,410,016 A | 4/1995 | Hubbell et al. .............. 528/354 |
| 5,446,091 A | 8/1995 | Rhee et al. ................. 525/54.1 |
| 5,455,027 A | 10/1995 | Zalipsky et al. |
| 5,462,976 A | 10/1995 | Matsuda et al. ............... 522/74 |
| 5,464,929 A | 11/1995 | Bezwada et al. ............ 528/361 |
| 5,475,052 A | 12/1995 | Rhee et al. ................. 525/54.1 |
| 5,514,379 A | 5/1996 | Weissleder et al. .......... 424/426 |
| 5,527,864 A | 6/1996 | Suggs et al. ................. 525/444 |
| 5,529,914 A | 6/1996 | Hubbell et al. .............. 435/182 |
| 5,567,435 A | 10/1996 | Hubbell et al. .............. 424/426 |
| 5,580,923 A | 12/1996 | Yeung et al. ................ 525/54.1 |
| 5,583,114 A | 12/1996 | Barrows ....................... 514/21 |
| 5,605,938 A | 2/1997 | Roufa et al. ................... 514/59 |
| 5,614,587 A | 3/1997 | Rhee et al. ................. 525/54.1 |
| 5,643,464 A | 7/1997 | Rhee et al. .................. 210/748 |
| 5,702,717 A | 12/1997 | Cha et al. .................... 424/425 |
| 5,711,958 A | 1/1998 | Cohn et al. ................. 424/423 |
| 5,744,545 A | 4/1998 | Rhee et al. ................. 525/54.1 |
| 5,752,974 A | 5/1998 | Rhee et al. .................. 606/214 |
| 5,786,421 A | 7/1998 | Rhee et al. ................. 525/54.1 |
| 5,801,033 A | 9/1998 | Hubbell et al. .............. 435/182 |
| 5,807,581 A | 9/1998 | Rosenblatt et al. .......... 424/484 |
| 5,834,274 A | 11/1998 | Hubbell et al. .............. 435/177 |
| 5,858,746 A | 1/1999 | Hubbell et al. .............. 435/177 |
| 5,874,500 A | 2/1999 | Rhee et al. ................. 525/54.1 |
| 5,936,035 A | 8/1999 | Rhee et al. ................. 525/54.1 |
| 5,962,006 A | 10/1999 | Southard et al. ............. 424/426 |
| 5,986,043 A | 11/1999 | Hubbell et al. .............. 528/354 |
| 6,051,248 A | 4/2000 | Sawhney et al. |
| 6,051,648 A | 4/2000 | Rhee et al. ................. 525/54.1 |

(Continued)

FOREIGN PATENT DOCUMENTS

WO WO 96/03159 2/1996

(Continued)

OTHER PUBLICATIONS

Boyers et al., "Reduction of postoperative pelvic adhesions in the rabbit with Gore-Tex surgical membrane," *Fertil. Steril.*, 49(6):1066 (1988).

(Continued)

*Primary Examiner*—Edward J. Webman
(74) *Attorney, Agent, or Firm*—Patterson, Thuente, Skaar & Christensen, P.A.

(57) ABSTRACT

Methods are provided for forming hydrogel barriers in situ that adhere to tissue and prevent the formation of post-surgical adhesions or deliver drugs or other therapeutic agents to a body cavity. The hydrogels are crosslinked, resorb or degrade over a period of time, and may be formed by free radical polymerization initiated by a redox system or thermal initiation, or electrophilic-neutrophilic mechanism, wherein two components of an initiating system are simultaneously or sequentially poured into a body cavity to obtain widespread dispersal and coating of all or most visceral organs within that cavity prior to gelation and polymerization of the regional barrier. The hydrogel materials are selected to have a low stress at break in tension or torsion, and so as to have a close to equilibrium hydration level when formed.

33 Claims, No Drawings

U.S. PATENT DOCUMENTS

| | | | |
|---|---|---|---|
| 6,086,907 A | 7/2000 | Goldberg et al. | 424/423 |
| 6,121,341 A * | 9/2000 | Sawhney et al. | 522/84 |
| 6,129,761 A | 10/2000 | Hubbell | 623/11 |
| 6,133,325 A | 10/2000 | Schwartz et al. | 514/781 |
| 6,136,333 A | 10/2000 | Cohn et al. | 424/423 |
| 6,153,211 A | 11/2000 | Hubbell et al. | 424/426 |
| 6,162,241 A | 12/2000 | Coury et al. | |
| 6,201,065 B1 | 3/2001 | Pathak et al. | |
| 6,214,966 B1 | 4/2001 | Harris | 528/322 |
| 6,258,351 B1 | 7/2001 | Harris | 424/78.3 |
| 6,306,922 B1 | 10/2001 | Hubbell et al. | 522/71 |
| 6,465,001 B1 | 10/2002 | Hubbell et al. | |

FOREIGN PATENT DOCUMENTS

| | | |
|---|---|---|
| WO | WO98/12274 | 3/1998 |
| WO | WO 98/12274 | 3/1998 |
| WO | WO 98/35631 | 8/1998 |
| WO | WO 99/08718 | 2/1999 |
| WO | WO 99/14259 | 3/1999 |

OTHER PUBLICATIONS

Holtz, "Prevention and management of peritoneal adhesions," *Fertil. Steril.*, 41:497-507 (1984).

Nagaoka et al., "Interaction Between Blood Components and Hydrogels with Poly(oxyethylene) Chains," *Polymers as Biomaterials* (Shalaby et al., Eds.), Plenum Press, p. 381 (1983).

Sawhney et al., "Bioerodible hydrogels based on photopolymerized poly (ethylene glycol)-co-poly (α-hydrozy acid) diacrylate macromers," *Macromolecules*, 26: 581-587 (1993).

*Encylopedia of Pharmaceutical Technology* (Boylan & Swarbrick, Eds.), vol. 1, Dekker, New York, p. 465.

Bhatia, et al., "The Effect of Site of Implantation and Animal Age on Properties of Polydioxanone Pins," *J. Biomateri. Sci.*, Polym. Ed., Bamford, C.H. et al., eds., 6(5):435 (1994).

Jarrett et al., "Bioabsorable Hydrogel Tissue Barrier: In Situ Gelatin Kinetics," *Trans. Soc. for Biomater.*, vol. XVIII, 182 (1995).

Park et al., *Biodegradable Hydrogels for Drug Delivery*, Technomic Pub. Co., Lancaster, PA., 1993.

Park, "Enzyme-digestible swelling hydrogels as platforms for long-term oral drug delivery: synthesis and characterization," *Biomaterials*, 9:435-441 (1988).

Zalipsky et al., "Esterification of Polyethylene Glycols," *J. Macromol. Sci. Chem.*, A21 (6&7):839-845 (1984).

*Remington's Pharmaceutical Sciences*, 14th Ed., J.E. Hoover et al., eds., Mack Publishing Co., Easton, Pennsylvania (1970).

*The Drug, The Nurse, The Patient, Including Current Drug Handbook*, by Falconer et al., 1974-1976, published by Saunder Company.

*Medicinal Chemistry*, 3rd Ed., vol. 1 and 2, by Burger, A., ed., published by Wiley-Interscience Co.

Roland et al., "Recent Developments in Free-Radical Polymerizaiton-A Mini Review," *Progress in Organic Coatings*, 21:227-254 (1992).

Bhatia, S., "The Effect of Site of Implantation and Animal Age on Properties of Polydioxanone Pins," *J. Biomater. Sci., Polymer. Edn.*, Bamford, C.H. et al., eds. 6(5): 435-446.

Chung, R.P.-et al., "Recent Developments in Free-Radical Polymeriation—A mini Review," *Progress in Organic Coatings*, Funke, W. et al., eds., 21(4):227-254 (1992).

Shalaby, S.W., "Bioabsorbable Polymers," *Encyclopedia of Pharmaceutical Technology*, Swarbrick, J. et al., eds., Marcell Dekker, Inc. New York, 1:465-476 (1988).

PCT Search Results (5,266,326).

Sawhney et al., Optimization of Photopolymerized Bioerodible Hydrogel Properties for Adhesion Prevention, *J. Biomedical Materials Research*, (28)831-38, 1994.

Sawhney et al., Use of a Photopolymerized Biodegradable Hydrogel for the Reduction of Epidural Fibrosis in a Rat Laminectomy Model, Presented at the Surfaces in Biomaterials 1993 Symposium, Cambridge, MA, Sep. 1993.

US 6,214,374, 04/2001, Schmirler et al. (withdrawn)

\* cited by examiner

METHODS FOR FORMING REGIONAL TISSUE ADHERENT BARRIERS AND DRUG DELIVERY SYSTEMS

RELATED APPLICATIONS

This application is a continuation application of U.S. application Ser. No. 09/134,748, filed on Aug. 14, 1998 now U.S. Pat. No. 6,514,534, which is hereby incorporated by reference herein in its entirety.

FIELD OF THE INVENTION

The present invention relates to methods of forming polymeric barriers to prevent post-surgical tissue adhesion and the use of such barriers to deliver drugs.

BACKGROUND OF THE INVENTION

The formation of post-surgical adhesions involving organs of the peritoneal cavity and the peritoneal wall is a frequent and undesirable result of abdominal surgery. Surgical trauma to the tissue caused by handling and drying results in release of a serosanguinous (proteinaceous) exudate that tends to collect in the pelvic cavity. If the exudate is not absorbed or lysed within a short time following the surgery, it becomes ingrown with fibroblasts. Subsequent collagen deposition leads to adhesion formation.

Numerous previously known methods have been developed to attempt to eliminate adhesion formation, but with limited success. Such methods include lavage of the peritoneal cavity, administration of pharmacological agents, and the application of barriers to mechanically separate tissues. For example, Boyers et al., "Reduction of postoperative pelvic adhesions in the rabbit with Gore-Tex surgical membrane," *Fertil. Steril.*, 49:1066 (1988), describes the use GORE-TEX® (a registered trademark of W.L. Gore & Assocs., Inc., Newark, Del.), expanded PTFE surgical membranes to prevent adhesions. Holtz, "Prevention and management of peritoneal adhesions," *Fertil. Steril.*, 41:497–507 (1984) provides a general review of adhesion prevention. None of the methods described in those articles has been cost effective and efficacious in in vivo studies.

Most adhesion prevention strategies have focused on either pharmacological approaches or barrier approaches. Pharmacological approaches have mainly relied on the local instillation of drugs such as antiinflammatory or fibrinolytic compounds. The advantage of the pharmacological approach is that the drugs can have not only a local but also a regional effect. The regional effect is particularly useful because, although iatrogenic injury is associated with adhesion formation, it is often difficult to predict all of the sites that may have been traumatized or exposed to ischemia during surgery. For example, during open surgical procedures, tissue often may be subjected to long periods of desiccation and surgical handling.

The word "local" as used herein is meant to connote a specific site on a tissue or organ surface, which for example is felt to be at risk for adhesion formation. The term "regional" as used herein, is meant to connote the general cavity or space within which any of several organs are at risk for adhesion formation, but where it is for example, difficult to predict all the sites where such adhesions may form.

Instillation of drugs in regional spaces, such as the peritoneal cavity, has been widely adopted for the prevention of post-surgical adhesions. Unfortunately, most drugs administered in this fashion have a limited residence time at the site of instillation and are rapidly cleared. Also, delivery problems attributable to ischemia may reduce the effectiveness of the drugs. In addition, adhesions may develop not only due to surgical insults, but also due to a variety of pathologies and etiologies that may not be addressed using a pharmacological approach.

In view of the foregoing, it would be desirable to provide methods of preventing post-surgical tissue adhesion that overcome the drawbacks of previously known methods while providing the regional benefits obtained from pharmacological approaches.

Previously known barrier methods rely on the ability to interpose an inert or absorbable material in between organs at risk of formation of adhesions. A variety of materials have been used as barriers, including pentapeptides or elastin, trypsin treated gamma-irradiated amniotic membranes, polyesterurethane-polydimethylsiloxane, carboxymethylcellulose sponge, collagen etc. These previously known materials, however, have been used primarily in academic contexts and have not been developed as commercial products.

Commercially available local barriers, such as sold under the name INTERCEED™, a registered trademark of Johnson and Johnson, Inc., New Brunswick, N.J., SEPRA-FILM™, Genzyme Corp., Cambridge, Mass. and REPEL™ under development by Life Medical Corp., Edison, N.J., rely on interposing a barrier material that is absorbed within a 28 day period to reduce adhesion formation. These barriers, however, may have limited efficacy due to migration of the barriers from a local implantation site. Moreover, these barriers do not provide the regional effect observed with pharmacological barriers.

Barriers that may be applied as a liquid also have been used, such as hyaluronic acid based products such as SEPRACOAT™, marketed by Genzyme Corp., Cambridge, Mass. U.S. Pat. No. 5,140,016 to Goldberg et al. describes a method and composition for preventing surgical adhesions using a dilute solution of a hydrophilic polymer such as hyaluronic acid. U.S. Pat. No. 5,190,759 to Lindblad et al. describes a composition and method for prevention of adhesions using solutions containing dextran and hyaluronic acid. These liquid barriers are rapidly cleared from a body cavity after instillation and thus may not be effective in preventing adhesions. Instead, such compositions are more effective as tissue protecting solutions during surgery rather than for the prevention of post-surgical adhesions.

Previously known attempts to prolong the residence of flowable barriers have attempted to form lightly crosslinked liquid barriers that still retain their flow characteristics. Thus, for example, LUBRICOAT™, available from Lifecore Biomedical Inc., Chaska, Minn., is a ferric hyaluronate crosslinked slurry considered for adhesion prevention. This material has been found to have only limited efficacy, however, because the barrier tends to migrate from the application site. Thus, tissues that naturally appose each other still form adhesions.

Other natural and synthetic polymers also have been considered to prevent adhesion formation. U.S. Pat. No. 5,605,938 to Roufa et al. describes methods and compositions for inhibiting cell invasion and fibrosis using dextran sulfate. The patent teaches that anionic polymers effectively inhibit invasion of cells associated with detrimental healing processes. The materials described, however, are not covalently polymerized, do not have mechanical integrity and do not bind to tissue. Such materials also may interfere with normal wound healing during the postoperative period.

Hydrogels are materials which absorb solvents (such as water), undergo rapid swelling without discernible dissolution, and maintain three-dimensional networks capable of reversible deformation. Because of their high water content and biocompatibility, hydrogels have been proposed for use as barriers for adhesion prevention.

U.S. Pat. No. 4,994,277 to Higham et al. describes the use of xanthan gum for preventing adhesions, wherein the hydrogel is more viscous than blood and is soluble in aqueous solutions. The water solubility of that gel system, however, enhances clearing and migration of the barrier. U.S. Pat. No. 4,911,926 to Henry et al. describes a method and composition for reducing post-surgical adhesions using aqueous and non-aqueous compositions comprising a polyoxyalkylene block copolymer. The resulting thermoreversible gels are not covalently crosslinked and have no mechanical integrity, thus making the barrier readily susceptible to displacement from the application site. The foregoing materials have shown limited efficacy in clinical trials.

U.S. Pat. No. 5,126,141 to Henry describes a composition and method for post-surgical adhesion reduction with thermo-irreversible gels of polyoxyalkylene polymers and ionic polysaccharides. These aqueous gels are rendered thermally irreversible upon contact with a counter-ion. A serious drawback of such systems is the biodegradability and absorbability of such barriers. Because there is no clear mechanism for the degradation of these ionically crosslinked materials, the barriers may remain biostable for uncertain periods of time and adversely impact the patient's health.

A similar disadvantage exists with respect to the barrier system described in U.S. Pat. No. 5,266,326 to Barry et al. That patent describes the in situ modification of alginate to form a hydrogel in vivo. Ionically crosslinked polysaccharides such as alginate are not absorbable in humans since no enzyme exists in humans to degrade the β glycosidic linkages. Moreover, the high molecular weight of the alginates used (upwards of 200,000 Da) do not allow filtration through the kidneys. The inability to eventually biodegrade the material is considered a major drawback.

U.S. Pat. No. 4,911,926 to Henry et al. describes aqueous and nonaqueous compositions comprised of block polyoxyalkylene copolymers that form gels in the biologic environment to prevent post-surgical adhesion. Other gel forming compositions have been suggested for use in preventing post-surgical adhesion, including: chitin derivatives (U.S. Pat. No. 5,093,319 to Henry et al.); chitosan-coagulum (U.S. Pat. No. 4,532,134 to Higham et al.); and hyaluronic acid (U.S. Pat. No. 4,141,973 to Balazs).

U.S. Pat. No. 4,886,787 to de Belder et al. describes a method of preventing adhesion between body tissues by employing a degradable gel of a crosslinked carboxyl-containing polysaccharide. U.S. Pat. No. 5,246,698 to Leshchiner et al. describes biocompatible viscoelastic gel slurries formed from a hyaluronan or a derivative thereof. The foregoing crosslinked gels are not formed in situ, but rather formed outside the body and then implanted as flowable gels. While covalent crosslinking of these materials may prolong residence time of the barrier within a body cavity, because the barriers are not formed in situ they do not adhere to the tissues within the body cavity and present a risk of migration.

Covalently crosslinked hydrogels (or aquagels) have been prepared based on crosslinked polymeric chains of methoxy poly(ethylene glycol) monomethacrylate having variable lengths of the polyoxyethylene side chains. Interaction of such hydrogels with blood components has been studied. See, e.g., Nagaoka, et al., in *Polymers as Biomaterial* (Shalaby et al., Eds.), Plenum Press, p. 381 (1983). A number of aqueous hydrogels have been used in various biomedical applications, such as, for example, soft contact lenses, wound management, and drug delivery. However, methods used in the preparation of these hydrogels, and conversion of these hydrogels to useful articles, are not suitable for forming these materials in situ in contact with living tissues.

U.S. Pat. No. 5,462,976 to Matsuda et al. describes photocurable glycosaminoglycan derivatives, crosslinked glycosaminoglycans and the use of such materials for tissue adhesion prevention. These materials, however, require external energy sources for transformation.

U.S. Pat. No. 5,410,016 to Hubbell et al. describes free radical polymerizable and biodegradable hydrogels that are formed from water soluble macromers. The patent describes the prevention of post-surgical adhesions using a local photopolymerization method, which shares the same disadvantage of requiring an external energy source. The patent also describes materials that are polymerizable by other free radical mechanisms, such as thermal or redox types of initiation.

Although these latter types of polymerization may be effectively exploited for the formation of regional barriers, only local methods for prevention of adhesion are taught in Hubbell et al. Also, effective concentrations used for the formation of local barriers using the aforementioned materials have been in the 10%–30% macromer concentration range, reflecting the structural integrity required to prevent migration of a locally adherent barrier. Such concentrations of hydrogel are unsuitable for regional barrier formation for several reasons, including:

1. The amount of macromer solution required for a regional barrier formation is in the range of 200 ml–3000 ml. At a 10–30% concentration the macromer would approach its toxicity limits for human use.
2. The structural integrity of the hydrogels formed at the foregoing concentrations may result in adverse effects similar to those seen from adhesions themselves, for example, due to the mobility restrictions that may result on visceral organs. Thus, formation of regional barriers at such concentrations may lead to postoperative pain and bowel obstructions.
3. Since such hydrogels have been observed to have an equilibrium water content in the range of 2–8%, the additional hydration of a large hydrogel mass in the abdominal or pelvic cavity may constrict and deform organs and tissue and thus have adverse effects. See, e.g., Sawhney et al., "Bioerodible hydrogels based on photopolymerized poly(ethylene glycol)-co-poly(α-hydroxy acid) diacrylate macromers", *Macromolecules*, 26:581–587 (1993).

In view of the foregoing, it would be desirable to provide in situ formation of regional barriers by macromer solutions at concentrations close to the equilibrium hydration levels to reduce or prevent post-surgical adhesion formation.

It further would be desirable to provide methods that enable a surgeon to create a regional barrier with little reliance on skill and accuracy of placement, thereby overcoming some of the significant drawbacks of previously known local adhesion prevention barriers.

SUMMARY OF THE INVENTION

In view of the foregoing, it is an object of this invention to provide methods of preventing post-surgical tissue adhesion that overcome the drawbacks of previously known methods while providing the regional benefits obtained from pharmacological approaches.

It is another object of this invention to provide in situ formation of regional barriers by macromer solutions at concentrations close to equilibrium hydration levels, to reduce or prevent post-surgical adhesion formation.

It is a further object of the present invention to provide methods that enable a surgeon to create a regional barrier with little reliance on skill and accuracy of placement, thereby overcoming some of the significant drawbacks of previously known local adhesion prevention barriers.

It is yet another object of this invention to provide methods of delivering drugs or other bioactive molecules to organs within a body cavity using a tissue adherent hydrogel layer that has a predictable residence time.

These and other objects of the present invention are accomplished in accordance with the principles of the present invention by providing methods of using hydrogels to form regional barriers in situ to prevent the formation of post-surgical adhesions. The regional hydrogel layers of the present invention also may be used to deliver drugs or other therapeutic agents to the region of interest, typically a body cavity.

Several methods for the formation of regional adhesion barriers are described, in which any of a variety of water soluble macromeric precursors are used. The term "macromeric precursor" or "macromer" is meant to connote an oligomeric or polymeric molecule that contains functional groups that enable further polymerization. Preferably the functionality of a macromer molecule is >1 so that a crosslinked network or hydrogel results upon polymerization. Hydrogels that resorb or degrade over a period of time are preferred, and more preferably, those that resorb within one or a few months.

In a preferred method, a crosslinked regional barrier is formed in situ, for example, by free radical polymerization initiated by a redox system or thermal initiation, wherein two components of an initiating system are simultaneously, sequentially or separately instilled in a body cavity to obtain widespread dispersal and coating of all or most visceral organs within that cavity prior to gelation and crosslinking of the regional barrier. Once the barrier is formed, the organs remain isolated from each other for a predetermined period, depending upon the absorption profile of the adhesion barrier material.

Preferably, the barrier does not undergo significant hydration, and is selected to have a low stress at break in tension or torsion, so as to not adversely affect normal physiological function of visceral organs within the region of application. The barrier also may contain a drug or other therapeutic agent.

DETAILED DESCRIPTION OF THE INVENTION

Preferred macromers suitable for practicing the methods of the present invention include water soluble crosslinkable polymeric monomers that have a functionality >1 (i.e., that form crosslinked networks on polymerization) and that form biodegradable hydrogels. The in situ formed hydrogels of the present invention may be crosslinked using several types of initiating systems. Some of these initiating systems require an external energy source, for example, in the form of radiation, focused ultrasound, or other means. Photopolymerization using ultraviolet or visible radiation has been widely used to polymerize free radically crosslinkable materials.

Within an animal or human body, at the sites of localized disease, it is useful to control the polymerization process to reduce or prevent post-surgical adhesion. The location of post-surgical adhesion formation, however, often is not predictable, and occurs not at the site of iatrogenic intervention. Instead, the location of adhesions depends on many factors, including pre-existing disease, ischemia etc.

In accordance with the present invention, methods are provided that permit diffuse coating of wide and complicated tissue geometries to form "regional" barriers, by coating essentially all tissues in the region of intervention with an adherent crosslinked hydrogel barrier.

The process of the present invention is conceptually similar to "hydroflotation," which entails filling up a body cavity with a lubricious fluid to float the organs within the cavity in isolation of each other. In hydroflotation, the fluid is invariably rapidly absorbed and cleared, leading promptly to organ apposition and adhesion formation.

In accordance with the principles of the present invention, an in situ formed hydrogel is used to "float" the organs for substantially longer than is possible with hydroflotation methods. Whereas hydroflotation has been associated with fluidic imbalances in the patient resulting from the use of hyperosmolar fluids, the method of the present invention does not rely on osmolality. Instead, it is the crosslinked structure of the hydrogel that prolongs residence of the barrier within the body cavity. Thus, the precursor solutions and the resulting hydrogel barrier may be iso-osmolar with the surrounding physiological fluids, and do not create any fluidic imbalances.

For macromers that possess ethylenically unsaturated bonds, regional barriers may be formed for example, by a free radically initiated polymerization. This may be undertaken using chemically (such as a redox system) and thermally activated initiating systems. Photopolymerization processes may optionally be used, but such processes typically are better suited for a local polymerization approach as opposed to a regional one. This is so because some tissues and organs may not transmit light of the wavelength being used. Also, photopolymerization generally is restricted to a "spot-by-spot" approach, and is unsuitable when it may be difficult to predict where the adhesions are likely to originate.

Other means for polymerization of macromers to form regional barriers may also be advantageously used with macromers that contain groups that demonstrate activity towards functional groups such as amines, imines, thiols, carboxyls, isocyanates, urethanes, amides, thiocyanates, hydroxyls etc. that may either be naturally present in, on, or around tissue or may be optionally provided in the region as part of the instilled formulation required to effect the barrier.

Materials Suitable for Formation of Regional Barriers

Absorbable polymers, often referred to as biodegradable polymers, have been used clinically in sutures and allied surgical augmentation devices to eliminate the need for a second surgical procedure to remove functionally equivalent non-absorbable devices. See, e.g., U.S. Pat. No. 3,991,766 to Schmitt et al. and *Encyclopedia of Pharmaceutical Technology* (Boylan & Swarbrick, Eds.), Vol. 1, Dekker, New York, p. 465 (1988). Interest in using such absorbable systems, with or without biologically active components, in medical applications has grown significantly over the past few years. Such applications are disclosed in Bhatia, et al., J. Biomater. Sci., Polym. Ed., 6(5):435 (1994); U.S. Pat. No. 5,198,220 to Damani; U.S. Pat. No. 5,171,148 to Wasserman, et. al.; and U.S. Pat. No. 3,991,766 to Schmitt et al.

Absorbable hydrogels that may be formed and crosslinked in situ to form a network are preferred materials for practicing the current invention. Synthesis and biomedical and pharmaceutical applications of absorbable or biodegradable hydrogels based on covalently crosslinked networks comprising polypeptide or polyester components as the enzymatically or hydrolytically labile components, respectively, have been described by a number of researchers. See, Jarrett et al., "Bioabsorbable Hydrogel Tissue Barrier: In Situ Gelatin Kinetics," Trans. Soc. Biomater., Vol. XVIII, 182 (1995); Sawhney et al., "Bioerodible hydrogels based on photopolymerized poly(ethylene glycol)-co-poly(α-hydroxy acid) diacrylate macromers", Macromolecules, 26:581–587 (1993); Park, et al., Biodegradable Hydrogels for Drug Delivery, Technomic Pub. Co., Lancaster, Pa., 1993; Park, "Enzyme-digestible swelling hydrogels as platforms for long-term oral drug delivery: synthesis and characterization," Biomaterials, 9:435–441 (1988).

Hydrogels described in the literature include, for example, those made of water-soluble polymers, such as polyvinyl pyrrolidone, which have been crosslinked with naturally derived biodegradable components such as those based on albumin.

Totally synthetic hydrogels are based on covalent networks formed by the addition polymerization of acrylic-terminated, water-soluble chains of polyether-poly(α-hydroxyester) block copolymers. These materials are among those preferred for practicing the present invention because they have been used for in vivo applications and have been demonstrated to be biocompatible. Details of compositions and methods to synthesize such materials have been described in U.S. Pat. No. 5,410,016 to Hubbell et al., which is incorporated herein by reference.

Preferred macromers for use in forming regional barriers for prevention of adhesion in accordance with the principles of the present invention include any of a variety of in situ polymerizable macromers that form hydrogel compositions absorbable in vivo. These macromers, for example, may be selected from compositions that are biodegradable, polymerizable, and substantially water soluble macromers comprising at least one water soluble region, at least one degradable region, and statistically more than 1 polymerizable region on average per macromer chain, wherein the polymerizable regions are separated from each other by at least one degradable region. The individual regions that comprise such macromers are described in detail below.

Water Soluble Regions

The water soluble region is selected from any of a variety of natural, synthetic, or hybrid polymers the group consisting of poly(ethylene glycol), poly(ethylene oxide), poly(vinyl alcohol), poly(allyl alcohol), poly(vinylpyrrolidone), poly(ethyleneimine), poly(allylamine), poly(vinyl amine), poly(aminoacids), poly(ethyloxazoline), poly(ethylene oxide)-co-poly(propyleneoxide) block copolymers, polysaccharides, carbohydrates, proteins, and combinations thereof.

Random copolymers of monomers that form water soluble polymers also may be used, for example, copolymers of vinyl amine and allyl alcohol. These types of random copolymers are preferred when the crosslinking reaction is mediated by nucleophilic or electrophilic functional groups. The water soluble region also may be selected from species that are capable of being rendered hydrophilic in a post-polymer reaction. For example, vinyl esters of carboxylic acids such as vinyl formate, vinyl acetate, vinyl monochloroacetate, and vinyl butyrate, may be copolymerized with the afore-described copolymerizable macromolecular monomers. Subsequent to the copolymerization reaction, the polymeric backbone (containing repeating monomeric units of these vinyl esters of carboxylic acids) may be rendered hydrophilic by hydrolysis to the resulting polyvinyl alcohol. In other words, the polymeric backbone comprises a polyvinyl alcohol.

Suitable species that may be polymerized and used in preparing the hydrophilic polymeric backbone of the macromers useful in the present invention include:

acrylic and methacrylic acid;

water-soluble monoesters of acrylic and methacrylic acid in which the ester moiety contains at least one hydrophilic group such as a hydroxy group, i.e., the hydroxy lower alkyl acrylates and methacrylates, typical examples of which include:

2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, diethylene glycol monomethacrylate, diethylene glycol monoacrylate, dipropylene glycol monomethacrylate, and dipropylene glycol monoacrylate;

water-soluble vinyl monomers having at least one nitrogen atom in the molecule, examples of which include:

acrylamide, methacrylamide, methylolacrylamide, methylolmethacrylamide, diacetone acrylamide N-methylacrylamide, N-ethylacrylamide, N-hydroxyethyl acrylamide, N,N-disubstituted acrylamides, such as N,N-dimethylacrylamide, N,N-diethylacrylamide, N-ethylmethylacrylamide, N,N-dimethylolacrylamide, and N,N-dihydroxyethyl acrylamide heterocyclic nitrogen containing compounds such as N-pyrrolidone, N-vinyl piperidone, N-acryloylpyrriolidone, N-acryloylpiperidine, and N-acryloylmorpholene; and cationic functional monomers, for example, vinyl pyridene quaternary ammonium salts and dimethyl aminoethyl methacrylate quaternary ammonium salts.

Suitable hydrophobic copolymerizable monomers also may be interpolymerized with hydrophobic copolymerizable macromolecular monomers and the aforementioned hydrophilic copolymerizable comonomers, so long as the ultimate products of biodegradation are water soluble. Hydrophobic species may include the alkyl acrylates and methacrylates, e.g., methylacrylate or methylmethacrylate, ethylacrylate or ethylmethacrylate, propylacrylate or propylmethacrylate, butylacrylate or butylmethacrylate, butylacrylate being preferred. Other suitable hydrophobic copolymerizable comonomers include vinyl chloride, vinylidene chloride, acrylonitrile, methacrylonitrile, vinylidene cyanide, vinyl acetate, vinyl propionate, and vinyl aromatic compounds such as styrene and alpha-methylstyrene, and maleic anhydride.

Degradable Regions

The degradable region is selected from any of a variety of polymers that undergo either hydrolytic, enzymatic, or thermal decomposition by bond scission of linkages so as to produce ultimately soluble and physiologically cleared molecules. Preferable biodegradable polymers, oliogomers or even single moieties can be selected from the group consisting of poly(α-hydroxy acids), poly(lactones), poly(amino acids), peptide sequences, oligonucleotides, poly(saccharides), poly(anhydrides), poly(orthoesters), poly(phosphazenes), and poly(phosphoesters), poly(urethanes), poly(amides), poly(imines), poly(esters), phosphoester linkages and combinations, copolymers, blends, etc. In some cases the water soluble and the degradable region may be one and the same, for example, in the case of proteins and poly(saccharides) that are degraded by naturally existing enzymes within the body.

Polymerizable Regions

The polymerizable end groups in these macromers may consist of groups that either react within themselves, with added excipients, or with the surface of tissue to form tissue protective coatings that function as regional barriers. Preferable end groups that mainly react within themselves may be selected from ethyleneically unsaturated functional groups such as acrylate, allyl, vinyl, methacrylate, cinnamate, or other ethylenically unsaturated functional groups.

Polymerizable groups may be selected from nucleophilic groups and their salts that react further, for example, with acylating agents. Useful nucleophilic groups may include primary, secondary, tertiary, or quaternary amino, amide, urethane, urea, hydrazide or thiol groups. These functional groups may be present along the main chain of the water soluble macromer or present only at the end groups. When they are present along the main chain of the macromer, they may be evenly spaced, as in a block copolymer, or they may be randomly spaced.

For example, Shearwater Polymers, Huntsville, Ala., sell p-PEGs which contain pendant functional groups. optionally these groups may be spaced from the polymeric main chain (either at the chain ends or along the backbone) by spacer groups that may contain ester linkages. The preparation of macromers containing amino acid esters of PEG is described, for example, in Zalipsky et al., "Esterification of Polyethylene Glycols," *J. Macromol. Sci. Chem.*, A21:839 (1984). The presence of such linkages can impart desirable properties such as speed of polymerization and predictable instability of the linkage.

Nucleophilic functional group-containing macromers optionally may be mixed with electrophilic group-containing macromers to rapidly initiate polymerization. It should be noted that several nucleophilic and electrophilic functional groups are naturally present in proteins, polysaccharides, glycosaminoglycans, and oligonucleotides that constitute tissue, cells, and organs and thus both nucleophilic and electrophilic macromers may react with appropriate naturally occurring functional groups in the absence of any additional externally added macromers.

For purposes of the present invention, however, reaction rates are more predictable and the resulting hydrogel will have more predictable properties if both components are added externally so as to initiate polymerization and formation of the hydrogel. Electrophilic groups that may be useful to react with the aforementioned nucleophilic groups may include carboxyl groups that may or may not be separated from the polymeric main chain (either at the chain ends or along the backbone) by spacer groups that may contain ester linkages (for example esters of succinic acid, carboxymethyl esters, esters of propionic, adipic, or amino acids), among others.

Other useful groups include isocyanate, thiocyanate, N-hydroxy succinamide esters such as succinamide as well as succinamide groups that are spaced by groups such as esters or amino acids, among others such as succinimidyl succinates, succinimidyl propionates, succinimidyl succinates, succinimidyl esters of carboxymethylated water soluble polymers, benzotriazole carbonates, and any of a variety of carbodiimides also may be selected. PEG succinimidyl succinates, PEG succinimidyl propionates, succinimidyl esters of amono acid or carboxymethylated PEG, and PEG succinamidyl succinamides are particularly suitable as electrophilically active macromers that react with nucleophilic group-containing macromers due to their high reactivity at physiological pH and speed of polymerization.

Other useful electrophilic macromers may contain functional groups such as glycidyl ethers (or epoxides) or hydroxyl group containing polymers that have been activated with 1,1,-carbonyl diimidazole (for example PEG-oxycarbonylimidazole) or p-nitrophenyl chlorocarbonates (e.g., PEG nitrophenyl carbonate), tresylates, aldehydes and isocyanates. Other groups reactive towards nucleophilic moieties may include for example anhydrides.

Thus, for example, a polymer of maleic anhydride when copolymerized with allyl or vinyl group containing water soluble polymers (such that the vinyl or allyl or other ethylenically unsaturated functionality is 1 per molecule or lower) forms a water soluble co-polymer that contains anhydride groups along the backbone. These anhydride groups are reactive towards any of the various nucleophilic groups mentioned hereinabove. Other electrophilic groups, that are more selective towards specific nucleophiles (such as sulfahydryl groups), also may be used, such as vinylsulfone, maleimide, orthopyridyl disulfide or iodoacetamide containing macromers.

It is to be understood that more than one type of electrophilic group or nucleophilic group may be present as a part of a macromer chain, so that multiple levels of reactivities may be built into the materials. In fact, both electrophilic and nucleophilic groups may be built into the same molecule and the solution prepared at a pH where the reactivity between these functional groups is low. A second solution that restores the appropriate pH upon mixing then may be added to initiate the crosslinking reaction.

Also, the concentration and number of the functional groups may be varied to obtain different rates of reactivity. The pH of the solutions may be varied to control rates of reaction, and the properties of the resulting crosslinked hydrogel also may be tailored by appropriate selection of the reactive macromers. For example, a higher molecular weight between crosslinks may lead to the formation of a lower modulus and more flexible hydrogel.

Delivery of Bioactive Species

The regional barriers of the present invention further may have bioactive molecules either dissolved or dispersed within them. The dispersed or dissolved drugs may be present as a particulate suspension, that either may or may not further be contained in a secondary containment membrane or coating, microspheres, or microcapsule. The materials for such secondary coating and containment also may be selected from any of a variety of biodegradable natural or synthetic hydrophobic materials that provide resistance to diffusion of small molecules, especially water soluble small molecules.

The biologically active molecules may include proteins (including growth factors and enzymes that may demonstrate bioactivity), carbohydrates, nucleic acids (both sense and antisense as well as gene fragments for gene therapy), organic molecules, inorganic biologically active molecules, cells, tissues, and tissue aggregates. Biologically active molecules may include any of the beneficial drugs as are known in the art, and described, for example, in *Pharmaceutical Sciences*, by Remington, 14th Ed., 1979, published by Mack Publishing Co.; *The Drug, The Nurse, The Patient, Including Current Drug Handbook*, by Falconer et al., 1974–1976, published by Saunder Company; and *Medicinal Chemistry*, 3rd Ed., Vol. 1 and 2, by Burger, published by Wiley-Interscience Co.

The drugs selected may serve to act against an underlying pathological condition that is suspected to contribute to the formation of adhesions, such as drugs that interfere with the polymerization of fibrin, serve as anticoagulants (such as heparin, hirudin, etc.) or act to dissolve fibrin clots or disrupt the native fibrinogen (such as tissue plasminogen activator, urokinase, streptokinase, streptodornase, ancrod, etc). Drugs having an antiinflammatory effect may be used, such as medroxyprogestrone acetate, which has been observed to reduce postoperative adhesion formation in animal studies. Other antiinflammatory compounds such as antibodies to IL-6, IL-1, TNF-α, and TGF-β have demonstrated efficacy as well.

Preferably, the drugs are directed to a process unique to adhesion formation, and which does not disrupt normal healing. For example, pentoxifylline, a drug used to treat intermittent claudication, and calcium channel blockers, such as verapamil, have been shown to reduce postoperative adhesion formation. It is thus expected that the delivery of one or more therapeutic compounds in a hydrogel-based regional barrier capable of controlled release may further enhance the prevention of postoperative adhesions. Thus, drugs that may be advantageously delivered using the regional barrier of the present invention include antiinflammatory compounds, antifibrinolytics, targeted modulators that interfere with the pathways of adhesion formation, such as IL-10 and antibodies to various cytokines, and immunomodulators.

Drugs delivered by the regional barrier also may serve to supplement the overall therapeutic regimen for the particular patient by delivering a drug or a combination of drugs that address another disease state. For example, physiologically active materials or medicinal drugs, such as agents affecting the central nervous system, antiallergic agents, cardiovascular agents, agents affecting respiratory organs, agents affecting digestive organs, hormone preparations, agents affecting metabolism, antitumor agents, antibiotic preparations, chemotherapeutics, antimicrobials, local anesthetics, antihistaminics, antiphlogistics, astringents, vitamins, antifungal agents, peripheral nervous anesthetics, vasodilators, crude drug essences, tinctures, crude drug powders, immunosuppressants, hypotensive agents, and the like may be delivered.

Drugs that are delivered using the regional barriers of the present invention may include both water soluble as well as partially water soluble or even lipophilic drugs. The drugs may be small molecules or macromolecular in nature. Particular water-soluble polypeptides which may be used in this invention are, for example, oxytocin, vasopressin, tissue plasminogen activator, urokinase, and other fibrinolytic enzymes, adrenocorticotrophic hormone (ACTH), epidermal growth factor (EGF), transforming growth factor antagonists, prolactin, luliberin or luteinizing hormone releasing hormone (LH-RH), LH-RH agonists or antagonists, growth hormone, growth hormone releasing factor, insulin, somatostatin, bombesin antagonists, glucagon, interferon, gastrin, tetragastrin, pentagastrin, urogastrone, secretin, calcitonin, enkephalins, endomorphins, angiotensins, renin, bradykinin, bacitracins, polymyzins, colistins, tyrocidin, gramicidines, and synthetic analogues and modifications and pharmaceutically-active fragments thereof, monoclonal antibodies and soluble vaccines.

The water-soluble drugs that may be delivered by this method are not specifically limited. Examples include peptides having biological activities, other antibiotics, antitumor agents, antipyretics, analgesics, anti-inflammatory agents, antitussive expectorants, sedatives, muscle relaxants, antiepileptic agents, antiulcer agents, antidepressants, antiallergic agents, cardiotonics, antiarrhythmic agents, vasodilators, hypotensive diuretics, antidiabetic agents, anticoagulants, hemostatics, antituberculous agents, hormone preparations, narcotic antagonists, bone resorption inhibitors, angiogenesis inhibitors and the like.

Examples of antitumor agents include bleomycin hydrochloride, methotrexate, actinomycin D, mitomycin C, vinblastine sulfate, vincristine sulfate, daunorubicin hydrochloride, adriamycin, neocarzinoszatin, cytosine arabinoside, fluorouracil, tetrahydrofuryl-5-fluorouracil krestin, picibanil, lentinan, levamisole, bestatin, azimexon, glycyrrhizin, poly I:C, poly A:U, poly ICLC, cisplatin and the like.

The terms "cytokine" and "growth factor" are used to describe biologically active molecules and active peptides (which may be either naturally occurring or synthetic) that aid in healing or regrowth of normal tissue, including growth factors and active peptides. The function of cytokines is two-fold: (1) to incite local cells to produce new collagen or tissue, or (2) to attract cells to a site in need of correction. For example, one may incorporate cytokines such as interferons (IFN), tumor necrosis factors (TNF), interleukins, colony stimulating factors (CSFs), or growth factors such as osteogenic factor extract (OFE), epidermal growth factor (EGF), transforming growth factor (TGF) alpha, TGF-β (including any combination of TGF-βs), TGF-β1, TGF-β2, platelet derived growth factor (PDGF-AA, PDGF-AB, PDGF-BB), acidic fibroblast growth factor (FGF), basic FGF, connective tissue activating peptides (CTAP), β-thromboglobulin, insulin-like growth factors, erythropoietin (EPO), nerve growth factor (NGF), bone morphogenic protein (BMP), osteogenic factors, and the like.

Suitable biologically-active agents for use in the present invention also include oxygen radical scavenging agents such as superoxide dismutase or anti-inflammatory agents such as hydrocortisone, prednisone and the like; antibacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, ribavirin, interferons and the like; antineoplastic agents such as methotrexate, 5-fluorouracil, adriamycin, taxol, taxotere, tumor-specific antibodies conjugated to toxins, tumor necrosis factor, and the like; analgesic agents such as salicylic acid, acetaminophen, ibuprofen, flurbiprofen, morphine and the like; local anesthetics such as lidocaine, bupivacaine, benzocaine and the like; vaccines such as hepatitis, influenza, measles, rubella, tetanus, polio, rabies and the like; central nervous system agents such as a tranquilizer, β-adrenergic blocking agent, dopamine and the like; growth factors such as colony stimulating factor, platelet-derived growth factors, fibroblast growth factor, transforming growth factor B, human growth hormone, bone morphogenetic protein, insulin-like growth factor and the like; hormones such as progesterone, follicle stimulating hormone, insulin, somatotropins and the like; antihistamines such as diphenhydramine, chlorphencramine and the like; cardiovascular agents such as digitalis, nitroglycerine, papaverine, streptokinase and the like; vasodilators such as theophylline, niacin, minoxidil, and the like; and other like substances.

The regional hydrogel barriers also may be used to delivery antitumor, antineoplastic, or anticancer agents to the body cavity, wherein multiple tumor sites exist and it may not be possible to accurately identify all sites of disease.

Physical and Mechanical Characteristics of Materials Suitable for Formation of Regional Barriers Materials suitable for use in forming the regional barriers in accordance with the present invention preferably have certain physical and mechanical attributes. These include safety, effectiveness at adhesion prevention, absorbability, non-inflammatoriness, compatibility with laparoscopic use, ease of use, efficacy at sites distant to surgery, lack of interference with normal healing, suitability as a pharmaceutical carrier, and conformity to tissue. While no adhesion barrier material may possess all of these properties, the materials described hereinabove satisfy many of these criteria.

In addition to the foregoing criteria, crosslinked materials suitable for use as regional tissue adherent adhesion barriers or drug delivery systems in accordance with the present invention should exhibit the following characteristics: (1) the materials should not obstruct the normal functioning of internal organs; and (2) these materials should not cause a substantial hydraulic imbalance after instillation and polymerization.

The first requirement ensures that, despite the extensive regional presence of the barrier throughout a body cavity, it will not impede normal tissue movement. Thus, even though the hydrogel barrier is crosslinked, it should not have the structural strength to adhere or bind organs together tenaciously. It is instead preferable that the barrier have weak cohesive strength and fail within the bulk of the material, rather than constrict organs to which it is applied. Desirable materials are expected to have stress at shear or tensile loading failure of less than 1 MPa. More preferably, the stress at failure should be between less than 300 KPa, and more preferably, less than 100 KPa.

The regional barriers need not form bulk hydrogels, but may form coatings on tissue upon instillation that may be thin and of the order of 1–1000 microns in thickness. In fact, the coating even may be formed as a surface modification of the tissue by instillation of macromers that have a reactivity to functional groups found on the surface of the tissues at risk for formation of adhesions. The instillation of the precursor solutions may be simultaneous or sequential, with a first solution coating tissue for some period of time and the subsequent solution being administered just prior to completion of the surgical procedure and closure of the surgical access points or incision.

The quantity of water contained within a hydrogel may be evaluated as "% Water Content," defined as:

$$\% \text{ Water Content} = 100 * \frac{(\text{Wet Hydrogel} - \text{Dry Hydrogel})}{\text{Wet Hydrogel}}$$

where:
Wet Hydrogel—the weight of wet hydrogel; and
Dry Hydrogel—the weight of dry hydrogel.

Hydrogels continue to absorb water from surrounding aqueous fluids until they reach an equilibrium level of hydration. During this process the addition increase in water content can be determined by measuring the % Hydration, which is defined as:

$$\% \text{ Hydration} = 100 * \frac{(\text{Wt. Hydrogel}_{Eq} - \text{Wt. Hydrogel}_F)}{\text{Wt. Hydrogel}_F}$$

where:
Wt. Hydrogel$_{Eq}$—the weight of hydrogel at equilibrium; and
Wt. Hydrogel$_F$—the weight of hydrogel at formation.

The requirement that the barrier material not create a hydraulic imbalance in situ arises from the relatively large volumes of such materials that are needed to form regional barriers as opposed to local barriers. It is expected, for example, that a typical use of regional barrier material in accordance with the present invention will involve the instillation of precursor materials in excess of 200 ml, possibly in excess of 500 ml, and in some cases, even as high as 3000 ml. Due to such relatively large volumes of instillates, it is important that the resulting regional barrier be relatively isotonic and near equilibrium hydration, i.e. it will not continue to absorb fluid from within the body cavity and induce fluid imbalance in the patient.

Similarly, the materials used to form the regional barriers of the present invention also should be close to the equilibrium level of hydration. Thus, the barrier will not appreciably increase in size by hydrating substantially after formation and thus will not impose undesirable mechanical obstructions within the body cavity. Accordingly, materials that hydrate less than 100% beyond their own weight in physiological aqueous solutions, at time of formation, are preferred. More preferable are materials that hydrate less than 50% of their own weight, and more preferably, materials that hydrate less than 20% beyond their initial weight at time of formation.

It is to be understood, based upon the foregoing discussion, that materials suitable for practicing the present invention should have many of the other beneficial properties expected of adhesion barrier materials, such as not eliciting an inflammatory response. If the barrier material generates a significant inflammation, it may enhance the formation of adhesions, rather than reducing or eliminating them. For example talc, which is considered to be an inflammatory material, is often used to create adhesions within the chest cavity by a regional instillation.

The hydrogel barriers formed in accordance with the methods of the present invention preferably are absorbed over time by natural physiological processes, so that the organs within the region of interest ultimately return to their original conformations. Absorption of the barrier material is defined herein as a lack of physical evidence of presence of the barrier at the application site. Preferably, the regional barriers of the present invention should absorb within 6 months, more preferably within 2 months, and most preferably within 1 month.

Free Radical Initiating Systems

Many previously known chemical systems that use free radical polymerization do not depend on external energy sources such as photoexcitation. Such systems advantageously may be used at physiological conditions of temperature and do not create physiologically toxic effects at the concentrations used. For example, Roland et al., "Recent Developments in Free-Radical Polymerization-A Mini Review," *Progress in Organic Coatings,* 21:227–254 (1992), presents an overview of the free radical polymerization process, with an emphasis on recent developments.

U.S. Pat. No. 4,511,478 to Nowinski et al. describes several types of oxidation-reduction initiators, including: (1) peroxides in combination with a reducing agent, e.g., hydrogen peroxide with ferrous ion or other transition metal ions, or benzoyl peroxide with an N,N-dialkylaniline or toluidine, and (2) persulfates in combination with a reducing agent, such as sodium metabisulfite or sodium thioslfate.

Specifically, ammonium persulfate, benzoyl peroxide, lauryl peroxide, tert-butyl hydroperoxide, tert-butyl perbenzoate, cumene hydroperoxide, dibenzoyl peroxide, tert-butyl peroctoate, tert-butyl peracetate, di-tert-amyl peroxide, ditert-butyl peroxide, tert-amyl perpivalate, butyl per-2-ethylhexanoate, tert-butyl perpivalate, tert-butyl perneodecanoate, tert-butyl perisononanoate, tert-amylperneodecanoate, di-2-ethyl-hexyl peroxydicarbonate, dicyclohexyl peroxydicarbonate, cumyl perneodecanoate, tert-butyl permaleate, 1,3-bis-(t-butylperoxyisopropyl)benzene, succinic acid peroxide, bis(1-hydroxycyclohexyl)-peroxide, isopropyl percarbonate, methyl ethyl ketone peroxide, and dicumyl peroxide, potassium ferricyanide, potassium permanganate, ceric sulfate, pinane hydroperoxide, di-isopropylbenzene hydroperoxide and other oxidizing compounds including combinations thereof with reducing agents, such as transition metal ions, sodium hyposulfite, sodium metabisulfite, sodium sulfide, sodium thiosulfate, hydrazine hydrate, sodium bisulfite or sodium thiosulfate, may be used. Sodium bisulfite alone may be used for polymerization.

Other initiators suitable for use in accordance with the methods of the present invention include, but are not limited to azo initiators. Preferred thermally active free radical polymerization initiators for use in the present invention may include, but are not limited to, diazodiisobutyrodinitrile, 2,2'-azobis-(isobutyronitrile), 2,2'-azobis(2,4-dimethylvaleronitrile), 2,2'-azobis(cyclohexanenitrile), 2,2'-azobis-(2-methylbutyronitrile), 2,2'-azobis(2,4-dimethyl 4-methoxyvaleronitrile), mixtures thereof and several like azo initiators such as those sold by Wako Chemical Co., Richmond, Va. Mixtures of two or more initiators also may be used, if desired.

Another group of catalysts, useful mainly for low temperature polymerization, include redox systems such as potassium persulfate-riboflavin, potassium persulfate-sodium bisulfite. Various compounds such as N,N,N',N-tetramethylethylenediamine and dimethyl toluidine may be used to accelerate the effect of the catalysts. Other suitable catalyst(s) and accelerant(s) may be used to catalyze the polymerization.

Inhibitors of Free Radical Polymerization

Free radical-inhibitors are generally used in the production, transportation and/or storage of systems that are reactive via free radicals to definitely exclude that the system will undergo premature reaction. With respect to the foregoing polymerizable materials, the addition of numerous compounds and/or systems that function as free radical-inhibitors are known, including, for example, hydrides such as lithium aluminum hydride, calcium hydride or sodium borohydride.

Further known examples serving this purpose are phenols, phenol derivatives, hydroquinone and hydroquinone derivatives or, especially, phenothiazine. As typical examples there may be mentioned cumene, hydroquinone, 2,6-di-tert-butyl-p-cresol, BHT, BRA, anisole, 2,6-di-tert-butyl-4-methoxyphenol, bis(2-hydroxy-3-tert-butyl-5-methylphenyl)methane, bis(3,5-di-tert-butyl- 4-hydroxyphenyl)methane, bis(2-hydroxy-3-tert-butyl-5-methylphenyl)sulfide, bis(3-tert-butyl-4-hydroxy-5-methyl-phenyl)sulfide, or also amines such as diphenylamine, N,N'-diphenyl-p-phenylene diamine, 2-phenylbenzimidazole, aniline, dinitrobenzene, 2-nitro-α-naphthol, tetraphenylethylene, triphenylmethane and vitamin E.

Methods of Instillation

In accordance with the methods of the present invention, macromer solutions used in forming regional barriers may be instilled by pouring, spraying (e.g., using two or more spray nozzles that simultaneously spray more than one solution into the region of interest), or by devices such as infusion catheters (e.g., dual lumen catheters or nozzles with mixing tips), funnel like devices, syringes, or bellows like devices with either dual chambers with a distal mixing tip, which is optionally attached, or with two separate devices that are either simultaneously or sequentially employed, etc.

The solutions may be selected so as to have active ingredients separated in two or more solutions that enable the polymerization upon mixing or on contact. Thus, for example, elements of a redox initiating system may be present in separate macromer solutions that either may be used simultaneously, sequentially or separately after an intervening interval of time to effect polymerization. In order to provide control of hydrogel formation, the barriers of the present invention may also include colored indicator substances such as phenol red (0.04–0.008%), thymol blue (0.04–0.1%), furoxone (0.02–0.4%), rivanol (0.45–0.75%) or picric acid (0.01–0.03%); or antibiotics such as tetracycline (0.7–0.17%), mithramycin (0.1–0.4%), or chlortetracycline (0.1–0.4%). (All percentages are w/v.)

As a result, a color change, such as a green color, will be observed after mixing or penetration of these colored substances (e.g., one is blue, other is yellow). The color changes also may be usefully observed as a result of pH change when two macromeric solution streams that are instilled into the body cavity are mixed, such macromeric solutions being selected such that the crosslinking reaction only occurs when an appropriate pH is reached, which is indicated by the presence of the pH sensitive calorimetric indicator.

Colored species also may be generated as part of the in situ reaction process. For example, the use of p-nitrophenyl activated PEG as a crosslinking molecule with a poly (amine) such as poly(ethyleneimine) will result in the generation of a yellow color due to the formation of p-nitrophenol as a reaction byproduct. This attribute of color appearance may be used to monitor successful deployment of the regional adhesion barrier.

The macromer solutions will typically be used at the end of the particular surgical procedure but may also be used during or even before undertaking the particular surgical procedure so as to serve as tissue protectants during the surgical procedure by hydrating and lubricating such tissues during the surgery. If thermal initiating systems are used, premature polymerization may be prevented by maintaining the solutions at low temperature so that polymerization occurs when physiological temperatures are attained upon instillation.

EXAMPLES

Example 1

A macromer is synthesized as described in U.S. Pat. No. 5,410,016 to Hubbell et al. The macromer may be an acrylated copolymer of poly(ethylene glycol) (M.W. 20,000) and dl-lactide (3–5 equivalents). The material is dissolved in water to form a solution that is 5% w/w, and the solution is divided into two parts. To part A is added enough hydrogen peroxide to give a 150 ppm concentration of $H_2O_2$. To part B is added enough of a ferrous gluconate salt to achieve a concentration of 3000 ppm. It may be verified that on mixing approximately equal parts of these two solutions, a flexible hydrogel is formed within 10 seconds of pouring into a mold, in the absence of activation by any external energy source.

Example 2

To assess the efficacy of the regional adhesion barrier of Example 1, the following experiment may be conducted. Twelve Sprague Dawley male rats having an average weight of 250 g are divided into two groups of 6 for treatment and control, respectively. The abdomen is shaved and prepared with a betadine solution. A midline incision is made under anesthesia. The cecum is located and 4 to 5 scrapes made on a region about 2×1 cm on one side of the cecum, using a 4×4 in gauze pad to produce serosal injury and punctuate bleeding. Other abdominal organs also may be allowed to desiccate for 10 minutes during this period. The abdominal incisions in these animals are closed using a continuous 4-0 silk suture for the musculoperitoneal layer and 7.5 mm stainless steel staples for the cutaneous layer. A topical antibiotic then is applied at the incision site.

The first group consists of 6 animals serving as controls without treatment, to confirm the validity of the model. The second group of 6 animals serves as a treatment with the application of the regional barrier. Approximately 5 cc of solution A described in Example 1 is applied to the injury site and over all the abdominal organs using a pipet. Care should be taken to ensure complete application to all organs. The muscular layer of the abdominal incision then is closed as above until the final suture tie is ready to be placed. At this time 5 cc of solution B from Example 1 above is instilled into the abdominal cavity. The walls of the abdominal cavity should be briefly massaged to ensure dispersal of the solutions and the closure of the abdominal and skin layers completed.

Three of the 6 animals in each group are sacrificed at the end of two days and 3 of the remaining animals in each group are sacrificed at the end of two weeks by $CO_2$ asphyxiation. The incisions are reopened and gross observations recorded. If adhesions are present, they should be scored for location, extent, and tenacity. The extent of adhesions should be reported as a percentage of the traumatized area of the cecum which forms adhesions with adnexal organs or the peritoneal wall. Tenacity of the adhesions is scored on a scale from 0 to 4: no adhesions—grade 0; tentative transparent adhesions which frequently separate on their own—grade 1; adhesions that give some resistance but can be separated by hand—grade 2; adhesions that require blunt instrument dissection to separate—grade 3; and dense thick adhesions which require sharp instrument dissection in the plane of the adhesion to separate—grade 4. It is expected that in the presence of the regional adhesion barrier, significant reduction in the extent of adhesion formation will occur.

Modifications and variations of the present invention, the macromers and polymeric compositions and methods of use thereof, will be obvious to those skilled in the art from the foregoing detailed description. Accordingly, various changes and modifications may be made therein without departing from the invention, and the appended claims are intended to cover all such changes and modifications that fall within the true spirit and scope of the invention.

What is claimed is:

1. A method for forming a regional hydrogel barrier in a patient, the method comprising:
    instilling a first component within a patient, wherein the first component comprises a pharmaceutically acceptable macromer having statistically more than one polymerizable region on average per molecule; and
    instilling a second component within the patient so that the second component contacts the first component, wherein the second component comprises an initiator selected from the group consisting of peroxides, persulfates, azo initiators, thermal initiators and redox initiators, thereby initiating the polymerization of the macromer in situ to form a regional hydrogel barrier that hydrates less than 100% in physiological solution compared to an initial weight of the hydrogel barrier.

2. The method of claim 1, wherein the first component and the second component arc simultaneously instilled into the patient.

3. The method of claim 1, wherein the first component and the second component are sequentially instilled into the patient.

4. The method of claim 1, wherein the pharmaceutically acceptable macromer further comprises at least one water soluble region.

5. The method of claim 4, wherein the pharmaceutically acceptable macromer further comprises at least one degradable region.

6. The method of claim 4, wherein the water soluble region is a member selected from the group consisting of poly(ethylene glycol), poly(ethylene oxide), poly(vinyl alcohol), poly(allyl alcohol), poly(vinylpyrrolidone), poly(ethyleneimine), poly(allylamine), poly(vinyl amine), poly(aminoacids), poly(ethyloxazoline), and poly(ethylene oxide)-co-poly(propyleneoxide) block copolymers.

7. The method of claim 4, wherein the water soluble region is a member selected from the group consisting of polysaccharides, carbohydrates and proteins.

8. The method of claim 5 wherein the degradable region is at least one member selected from the group consisting of poly(α-hydroxy acids), poly(lactones), poly(amino acids), peptide sequences, oligonucleotides, poly(saccharides), poly(anhydrides), poly(orthoesters), poly(phosphazenes), poly(urethanes), poly(amides), poly(imines), poly(esters) and phosphoester linkages.

9. The method of claim 1, wherein the peroxide and persulfate initiators are used in combination with a reducing agent.

10. The method of claim 1, wherein the polymerization of the macromer is accomplished by free radical polymerization.

11. The method of claim 10, wherein the free radical polymerization is initiated by a free radical polymerization initiator.

12. The method of claim 1, wherein the polymerizable region is at least one member selected from the functional group consisting of acrylate, allyl, vinyl, methacrylate and cinnamate.

13. A method of forming a regional hydrogel barrier in a patient, the method comprising:
    instilling a first component within the patient wherein the first component comprises a pharmaceutically acceptable macromer having statistically more than one polymerizable region on average per molecule; and
    instilling a second component within the patient that contacts the first component, wherein the second component is an initiator for initiating polymerization of the macromer in situ without the addition of external energy to form a regional hydrogel barrier that hydrates less than 100% in physiological solution compared to an initial weight of the hydrogel barrier.

14. The method of claim 13, wherein the first component and the second component are simultaneously instilled into the patient.

15. The method of claim 13, wherein the first component and the second component are sequentially instilled into the patient.

16. The method of claim 13, wherein the pharmaceutically acceptable macromer further comprises at least one water soluble region.

17. The method of claim 16, wherein the pharmaceutically acceptable macromer further comprises at least one degradable region.

18. The method of claim 16, wherein the water soluble region is a member selected from the group consisting of poly(ethylene glycol), poly(ethylene oxide), poly(vinyl alcohol), poly(allyl alcohol), poly(vinylpyrrolidone), poly(ethyleneimine), poly(allylamine), poly(vinyl amine), poly(aminoacids), poly(ethyloxazoline), and poly(ethylene oxide)-co-poly(propyleneoxide) block copolymers.

19. The method of claim 16, wherein the water soluble region is a member selected from the group consisting of polysaccharides, carbohydrates and proteins.

20. The method of claim 17, wherein the degradable region is at least one member selected from the group consisting of poly(α-hydroxy acids), poly(lactones), poly(amino acids), peptide sequences, oligonucleotides, poly(saccharides), poly(anhydrides), poly(orthoesters), poly(phosphazenes), poly(urethanes), poly(amides), poly(imines), poly(esters) and phosphoester linkages.

21. The method of claim 13, wherein the polymerizable region is at least one member selected from the functional group consisting of acrylate, allyl, vinyl, methacrylate and cinnamate.

22. The method of claim 13, wherein the polymerization of the macromer is accomplished by free radical polymerization.

23. The method of claim 22, wherein the free radical polymerization is initiated by a free radical polymerization initiator.

24. The method of claim 13, wherein the initiators are peroxide or persulfate initiators.

25. The method of claim 24, wherein the peroxide or persulfate initiators are used in combination with a reducing agent.

26. A regional hydrogel barrier for treating a patient comprising:
a hydrogel formed in a region of the patient comprising a pharmaceutically acceptable macromer crosslinked by an initiator selected from the group consisting of peroxides, persulfates, azo initiators, thermal initiators and redox initiators, wherein the macromer has before polymerization more than one polymerizable region on average per molecule, at least one water soluble region and at least one degradable region wherein the hydrogel hydrates less than 100% in physiological solution compared to an initial weight of the hydrogel barrier.

27. The hydrogel of claim 26, wherein the water soluble region is a member selected from the group consisting of poly(ethylene glycol), poly(ethylene oxide), poly(vinyl alcohol), poly(allyl alcohol), poly(vinylpyrrolidone), poly(ethyleneimine), poly(allylamine), poly(vinyl amine), poly(aminoacids), poly(ethyloxazoline), and poly(ethylene oxide)-co-poly(propyleneoxide) block copolymers.

28. The hydrogel of claim 26, wherein the water soluble region is a member selected from the group consisting of polysaccharides, carbohydrates and proteins.

29. The hydrogel of claim 26, wherein the degradable region is at least one member selected from the group consisting of poly(α-hydroxy acids), poly(lactones), poly(amino acids), peptide sequences, oligonucleotides, poly(saccharides), poly(anhydrides), poly(orthoesters), poly(phosphazenes), poly(urethanes), poly(amides), poly(imines), poly(esters) and phosphoester linkages.

30. A system for producing a regional hydrogel barrier within a patient, the system comprising:
a first component comprising a pharmaceutically acceptable macromer having statistically more than one polymerizable region on average per molecule;
a second component that includes at least one initiator that is a member selected from the group consisting of peroxides, persulfates, azo initiators, thermal initiators and redox initiators; and
an applicator for instilling the first component and the second component in situ in a regional area of the patient to form the regional hydrogel barrier.

31. The system of claim 30, wherein the applicator is adapted to instill the first component and the second component simultaneously.

32. The system of claim 30, wherein the applicator is adapted to instill the first component and the second component sequentially.

33. A method of forming a regional hydrogel barrier in a patient, the method comprising:
instilling a first component within the patient, wherein the first component comprises a pharmaceutically acceptable macromer having statistically more than one polymerizable region an average per molecule; and
instilling a second component within the patient that contacts the first component, wherein the second component is a means for initiating polymerization of the macromer in situ in a regional area of the patient without the addition of external energy to form a regional hydrogel barrier that hydrates less than 100% in physiological solution compared to an initial weight of the hydrogel barrier.

* * * * *